United States Patent [19]
Okayama et al.

[11] Patent Number: 5,580,526
[45] Date of Patent: Dec. 3, 1996

[54] ANALYTIC TEST SHEET FEEDER

[75] Inventors: Masao Okayama, Ryugasaki; Takao Terayama, Ushiku; Kazuo Honma, Ibaraki-ken; Hiroshi Ohki, Tsuchiura; Isao Shindo, Katsuta; Susumu Kai, Katsuta; Shigeo Mutou, Hitachiota, all of Japan

[73] Assignee: Hitachi, Ltd., Tokyo, Japan

[21] Appl. No.: 226,984

[22] Filed: Apr. 13, 1994

[30] Foreign Application Priority Data

Apr. 13, 1994 [JP] Japan .................. 5-085869

[51] Int. Cl.⁶ .................. G01N 35/00; B65H 3/00
[52] U.S. Cl. .................. 422/66; 422/63; 422/67
[58] Field of Search .................. 422/62, 63, 66, 422/68.1, 67; 436/44, 46, 171

[56] References Cited

U.S. PATENT DOCUMENTS 4,876,204  10/1989  Inoue et al. .................. 436/46
5,298,425  3/1994  Kuhn et al. .................. 436/43

FOREIGN PATENT DOCUMENTS

| 0166163 | 1/1986 | European Pat. Off. . |
|---|---|---|
| 0336126 | 10/1989 | European Pat. Off. . |
| 542260A1 | 5/1993 | European Pat. Off. . |
| 0542260 | 5/1993 | European Pat. Off. . |
| 0555711 | 8/1993 | European Pat. Off. . |
| 0597419 | 5/1994 | European Pat. Off. . |
| 3921392 | 1/1991 | Germany . |

*Primary Examiner*—N. Bhat
*Attorney, Agent, or Firm*—Antonelli, Terry, Stout & Kraus

[57] ABSTRACT

An analytic test sheet feeder comprises a cylindrical container 11 having an elongated through hole 15 formed in a side wall thereof for receiving a test sheet, a container support 18 which comprises an upper portion having a semi-cylindrical concave surface and a hole 20 formed in a central portion of the concave surface to permit a test sheet descending from the through hole of the container 11 to be taken out therethrough 20, and a test sheet delivering stage 31 which receives and delivers the test sheet descending from the through hole 15.

1 Claim, 5 Drawing Sheets

ANALYTIC TEST SHEET FEEDER

BACKGROUND OF THE INVENTION

The present invention relates to an analytic test sheet feeder for removing and supplying small strip or rod-like test sheets one by one, which feeder is suitable for extracting test sheets one by one with high reliability.

In clinical examinations in hospitals, analytic test sheets are often used for easily examining a plurality of analytic items in urine samples and blood samples. A test sheet has an elongated strip made of a plastic material or the like on which a plurality of testing pieces impregnated with reagents are adhered.

A known automatic test-sheet analyzer in which handling of such analytic test sheets is automated is disclosed in Japanese Patent Unexamined Publication No. 61-91571. This conventional-technique has a structure in which an arm having a test sheet holder is moved between a test sheet feeding mechanism, a sample table on which sample containers to immerse test sheets are placed, and a photometric mechanism, with colored test sheets being subjected to photometry. The test sheet feeding mechanism supplies test sheets one by one to a starting position of the test-sheet delivery by the arm.

In the foregoing test sheet feeding mechanism disclosed in Japanese Patent Unexamined Publication No. 61-91571, an elongated test sheet is supplied by sliding the bottom of a hopper. Consequently, when a curved test sheet is drawn out, other test sheets are apt to be caught between the wall and the bottom of the hopper, which results in a problem that smooth operation is hindered.

SUMMARY OF THE INVENTION

It is an object of the present invention to provide an analytic test sheet feeder which can automatically supply test sheets smoothly irrespective of the shape of the test sheets.

An analytic test sheet feeder according to this invention comprises container means having a cylindrical container which contains a plurality of analytic test sheets, with the cylindrical container having a through hole formed in a wall thereof so that a test sheet can be fitted in the through hole. A removal means reciprocates the cylindrical container to rotate around its own axis, with a test sheet being fitted in the through hole, and with a removal of the test sheet in the through hole out of the cylindrical container when a rotation of the cylindrical container is stopped. Delivery means deliver the test sheet to an outside supplying position on the test sheet feeder, and separation means separate the test sheets from one another when two or more test sheets are simultaneously removed and placed on the delivery means.

In place of the above-mentioned separation means, returning means may be provided for partly returning the plurality of test sheets removed, into the container means so as to remove them again.

The container means contains a plurality of analytic test sheets. The removing means extracts the test sheets one by one from the container means. When two or more test sheets are simultaneously removed by the removal means, the separation means separates the plural test sheets from one another by passing them in a narrow passage. The delivery means delivers each of the separated test sheets to an outside supplying position on the feeder.

The returning means in place of the separation means partly feeds back the plurality of test sheets removal by the removing means, and returns them into the container means. Thus, the test sheets are removed one by one again.

DETAILED DESCRIPTION OF THE PREFERRED EMBODIMENTS

Figures 6, 6A, 6B:
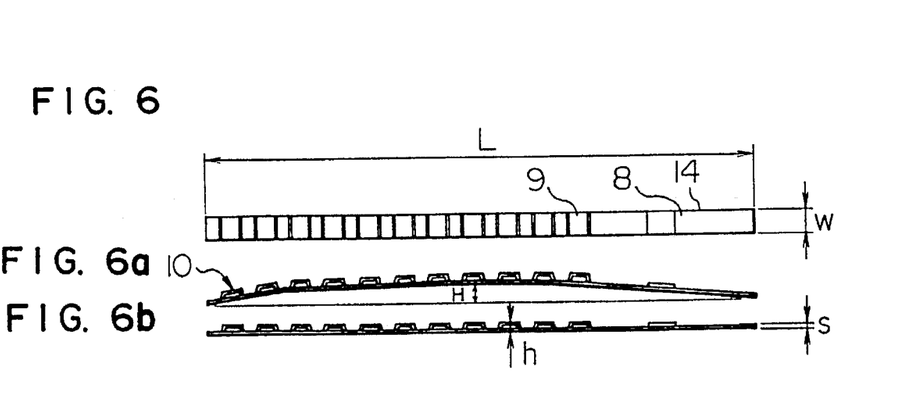
FIG. 6 is a top plan view showing one example of an analytic test sheet used in the test sheet feeder of the invention.
FIG. 6a is a side view of the analytic test sheet of FIG. 6 after being immersed in a sample.
FIG. 6b is a side view of the analytic test sheet of FIG. 6 prior to immersion in a sample.

As shown in FIG. 6, the test sheet 14 has an elongated plastic stick 8 of a length L to which a plurality of testing pieces 9 impregnated with reagents are adhered by thin mesh cloth 10. All these testing pieces 9 are immersed in a sample in a container at once, and thereafter they are drawn out of the sample container, thereby causing color reactions to progress on the testing pieces 9. Generally, each of the testing pieces 9 is about 5 mm square, and its thickness is 0.5 to 1.5 mm. The example of test sheet 14 shown in FIGS. 6, 6a, 6b has a length L of 120 mm, a width w of 5 mm and a thickness h (FIG. 6b) of 1.8 mm. When the test sheet 14 is immersed in a sample in a container, the mesh cloth 10 which fixes the testing pieces is shrunk, and the test sheet 14 is curved. Consequently, the test sheet 14 is curved in advance to have a height H (FIG. 6a) of 1 to 4 mm. The testing pieces 9 are made of filter paper or felt.

Figure 7:
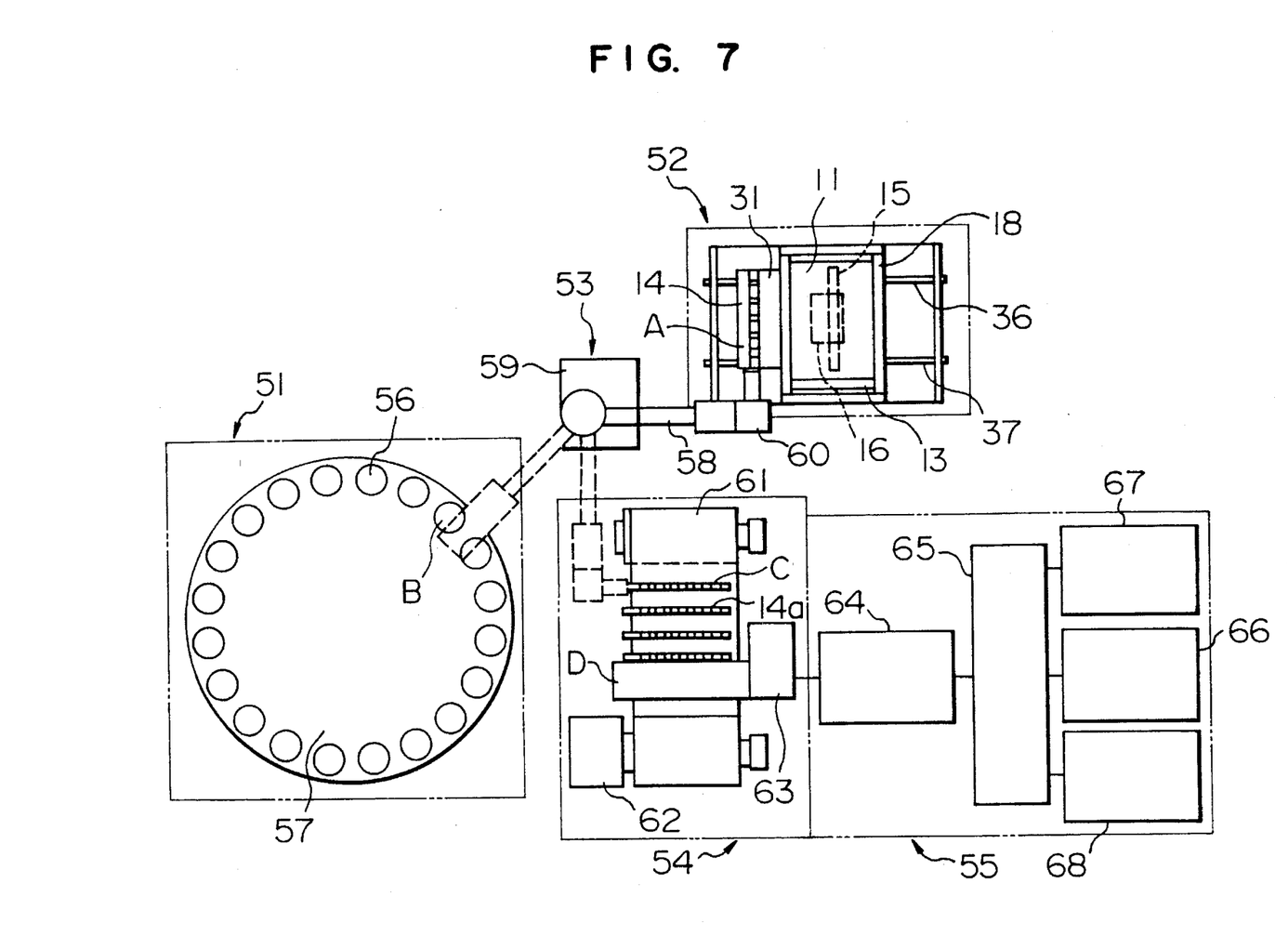
FIG. 7 is a diagrammatic view showing the entire structure of an analyzer according to one embodiment of the invention.
Figure 8:
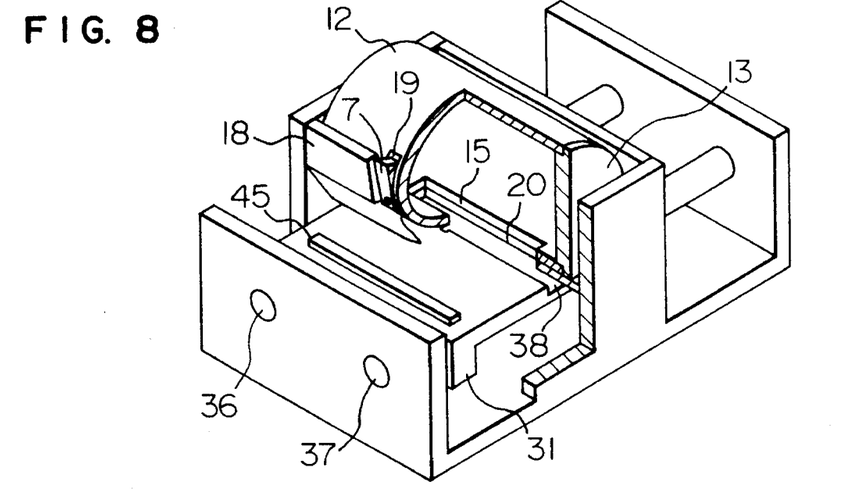
FIG. 8 is a partly broken-away view showing the appearance of the feeder of FIG. 1 when a stage is moved.

An automatic test sheet feeder 52 according to the present invention is applied to an apparatus for organic samples such as urine samples and blood samples. As one embodiment, an automatic analyzer of urine samples will be hereinafter described. The analyzer of the invention, as shown in FIG.

7, comprises an automatic test sheet feeder 52, sample positioning means 51, test sheet transfer means 53, measuring means 54 and a control/calculation unit 55. The control/calculation unit 55 not only controls operations of the mechanisms but also calculates data of the testing pieces of each analytic test sheet measured by a photometer 63, thus producing results of the measurement.

The sample positioning means 51 transfers containers 56 containing urine samples arranged on a turn table 57 successively to a test sheet immersing position B.

The automatic test sheet feeder 52 feeds analytic test sheets 14 to a predetermined outside supplying position A one by one from a cylindrical container 11 which contains a large number of, for example, 200 test sheets 14. Feed of the test sheets to the outside supplying position A is performed in synchronism with the operation cycle of the analyzer.

The test sheet transfer means 53 include an arm 58 which can be swung, a driving mechanism 59, and a test sheet holder 60 attached close to the distal end of the arm 58. The transfer means 53 holds, by the holder 60, a test sheet 14 fed to the outside supplying position A, delivers the test sheet 14 to the immersing position B, and immerses all the testing pieces 9 of the test sheet 14 in a sample in a sample container 56 located at the immersing position B while continuing to hold the test sheet 14. After immersion for a predetermined period of time, the test sheet 14 is drawn out of the container, delivered toward the measuring means 54, and released from the holder 60 when it reaches a test sheet mounting position C. Thereafter, the holder 60 is returned to the outside supplying position A of the test sheet feeder 52. By then, the next test sheet has been fed to the outside supplying position A. During the analysis, such operations are repeated.

In the measuring means 54, a roll of paper 61 is used for transferring a reacting test sheet 14a which has been received from the test sheet transfer means 53. By winding the rolled paper 61 by a take-up mechanism 62 at predetermined time intervals, the test sheet 14a, placed in the mounting position, is transferred to a photometric position D. The test sheet 14a is positioned at the photometric position D for photometry by the photometer 63 when a predetermined period of time elapses after the sample immersion. The photometer 63 includes a plurality of small-sized reflection type detectors comprising light sources which emit light beams having predetermined wavelengths corresponding to analytic items, and silicon photodiode light receiving elements. The plurality of detectors are arranged at positions corresponding to detecting positions of the surfaces of the testing pieces on the test sheet 14a. The photometer 63 measures intensities of reflected light beams from the surfaces of the testing pieces which have reacted and have changed color. Results of the measurement are passed through an A/D converter 64 of the control/calculation unit 55, subjected to data processing in a control unit 65, and indicated on liquid crystal display means 66 while printed by a printer 67.

The analytic operation with the above-described analyzer progresses in response to an input from an operation panel 68 in the control/calculation unit 55. Test sheets 14 which have been measured are rolled together with the rolled paper 6' by the take-up mechanism 62, so that they can be removed and disposed of with the rolled paper 6' after the completion of the measurement.

The structure of the automatic test sheet feeder 52 employed in the analyzer shown in FIG. 7 will be described more specifically with reference to FIGS. 1 to 5 and FIGS. 8 to 12.

Figure 3:
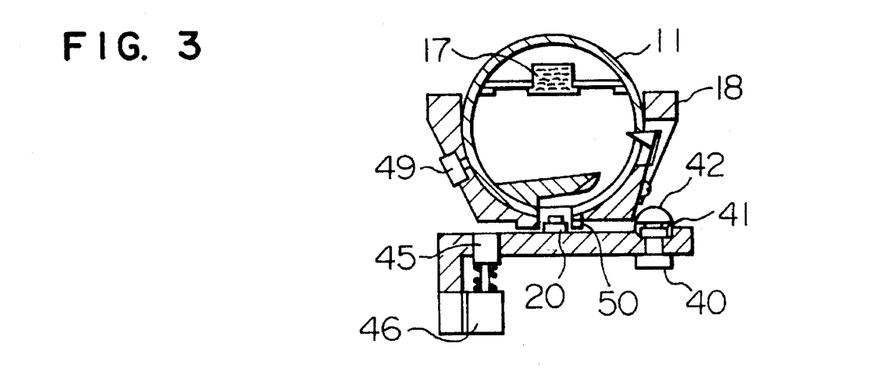
FIG. 3 is a cross-sectional view for explaining the operation of the feeder shown in FIG. 1.

The cylindrical container 11 which can contain a plurality of analytic test sheets comprises a container body 12 and a cover 13. The cover 13 which permits test sheets to be introduced or removed is provided at a location corresponding to the top or bottom of the cylindrical container 11. The container body 12 includes a shelf for containing a desiccant 17 (FIG. 3). A space between the bottom of the container body 12 and the cover 13 defines a test sheet containing chamber formed in such a manner that a distance between the bottom and the cover, i.e., a depth of the test sheet containing chamber, is slightly larger than the length L of the test sheets 14. Thus, when a plurality of, for example, 200 test sheets are arranged in the longitudinal direction and placed in the test sheet containing chamber, the test sheets will not extend in irregular directions even if the cylindrical container 11 is reciprocally rotated.

Figure 10:
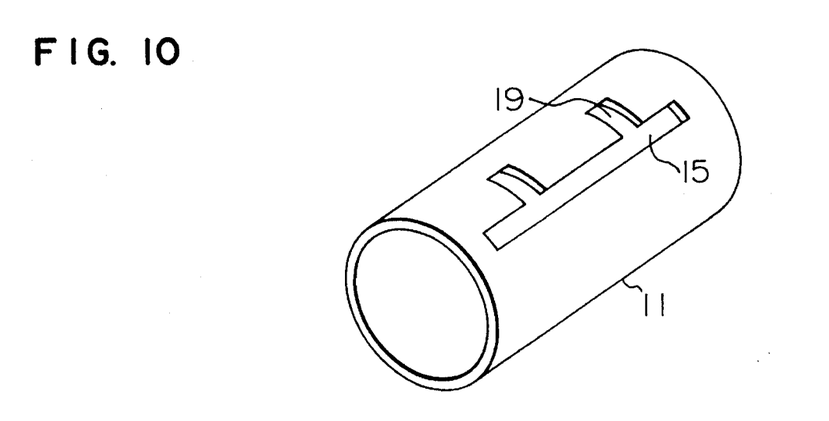
FIG. 10 is a perspective view showing the appearance of one example of a cylindrical container in the feeder of the invention.

A rectangular through hole 15, shown most clearly in FIG. 10 has a size and a shape such that each test sheet 14 can be closely fitted therein, and holes 19 (FIGS. 8 and 10) through which test sheet pressing springs 7 are passed, are formed in the curved wall of the cylindrical container 11, and the through hole 15 extends in parallel to a direction of the rotational axis (FIG. 10). The length of the through hole 15 is slightly larger than the length L of the test sheet 14, and the width of the through hole 15 is slightly larger than the width W (FIG. 6) of the test sheet 14. The depth of the through hole 15, i.e., the thickness of the curved wall, is substantially equal to the thickness h (FIG. 6b) of the test sheet 14. A guide member 16, which helps each test sheet 14 to be reliably fitted in the through hole 15, is provided on the side of the through hole 15 which is closer to the rotational axis, so as to cover the through hole 15. The guide member 16 includes a root portion fixed to the wall so as to introduce the test sheet 14 into the through hole 15 when the cylindrical container 11 is rotated counterclockwise but to prevent the test sheet 14 from entering into the through hole 15 when the cylindrical container 11 is rotated clockwise.

The cylindrical container 11 is slidably provided on a container support 18 for serving not only to prevent a test sheet from jumping out of the container but also to shut out the outside air. The test sheet pressing springs 7 for introducing the test sheet 14 beneath the guide member 16, as described before, are attached on the container support 18. By rotating the cylindrical container 11, the test sheet 14 is pressed beneath the guide member 16 and subsequently inserted into the through hole 15. When the through hole 15 of the cylindrical container 11 is located at the lowermost position, the rotation is stopped and a shutter mechanism 45 is moved down. A test sheet delivering stage 31 for delivering each test sheet dropped from the through hole 15 to the outside supplying position A is provided below the container support 18 and can be moved on guide shafts 36, 37. During this movement, the upper surface of the delivering stage 31 can be slid on the lower surface of the support 18.

Figure 9:
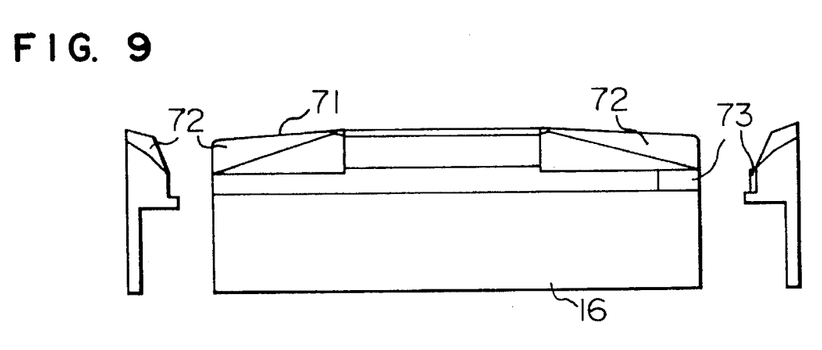
FIG. 9 is an exploded front view showing one example of a guide member in the feeder of the invention.
Figure 11:
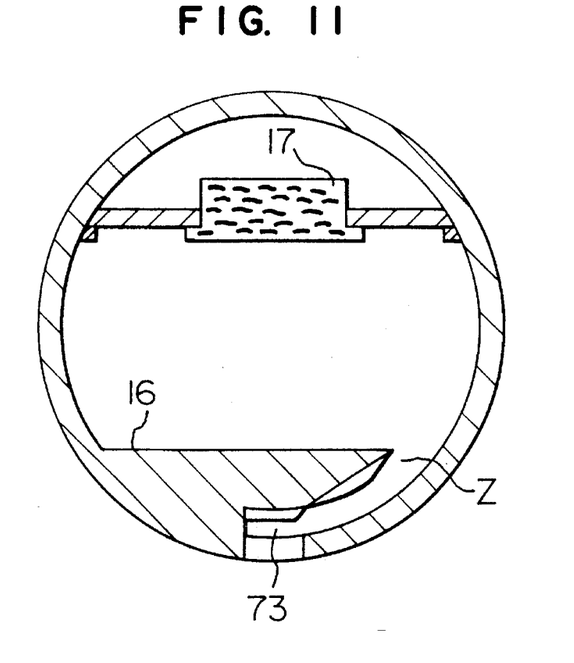
FIG. 11 is a cross-sectional view showing the cylindrical container and the guide member in the feeder of the invention.
Figure 12:
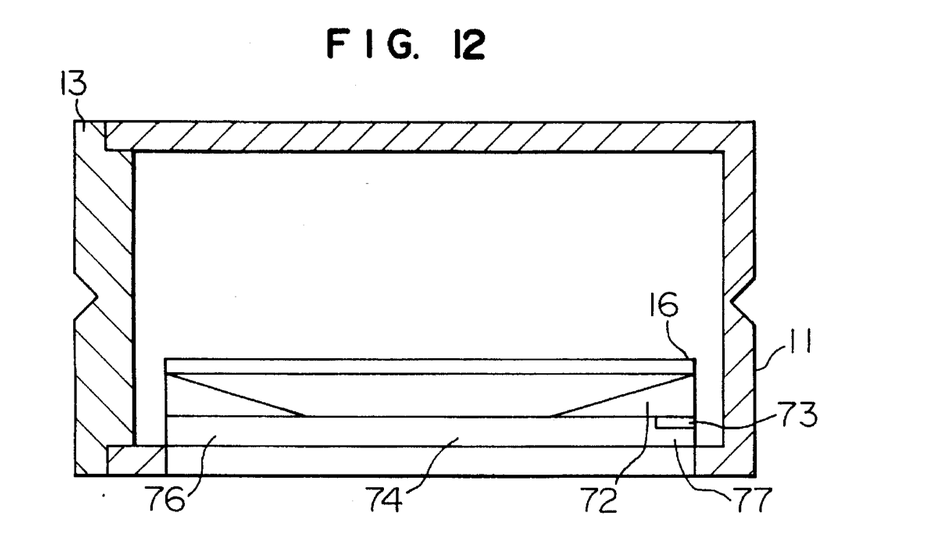
FIG. 12 is a vertical cross-sectional view showing the cylindrical container and the guide member in the feeder of the invention.

As shown in FIGS. 9, 11 and 12, in order to pass test sheets 14 one by one irrespective of bend of the test sheet 14 amounting to 1 to 4 mm, the gap between a central portion 74 of the guide member 16 (FIG. 12) and the inner wall of the container 11 is slightly larger than the thickness $\underline{h}$ (FIG. 6b) of the test sheets 14 and less than 2h which is twice the thickness h of the test sheets 14. Further, in order to facilitate passing of the bent test sheets 14, inlet portions 72 (FIG. 6a) of the guide member 16 on both ends are chamfered at an angle so that the gaps between the inlet portions 72 and the inner wall of the container 11 are wider than the height H (FIG. 6a) of the bent test sheets, and that the gaps between the inner edges of the chamfered portions on both ends and the inner wall of the container 11 are equal to the thickness $\underline{h}$ (FIG. 6b) of the test sheets. Moreover, the inlet gap Z (FIG. 11) between the guide member 16 and the inner wall of the container 11 is equal to ½ to 1/1 of the width W (FIG. 6) of the test sheets 14, thereby facilitating entering of each test sheet 14 beneath the guide member 16. The gap between a root portion of an extension of the guide member 16 and the upper edge of the through hole 15 is such that a distance of the gap at a portion 76 on the front side of the cylindrical container is greater than the thickness $\underline{h}$ (FIG. 6b) of one test sheet 14 and less than $2h$ which is twice the thickness of the test sheet, and that the distance of the gap at a portion 77 on the rear side of the cylindrical container is slightly less than the thickness of the test sheet by forming a stepped portion 73 (FIG. 9) on the rear-side portion 77. Thus, the surfaces of two test sheets 14 where the testing pieces 9 are not provided will not be superposed diagonally in the through hole 15 but the test sheets 14 can be smoothly introduced one by one into the through hole 15.

The cylindrical container 11 is reciprocally rotated by a pulse motor 25 (FIG. 5) which is a rotation drive source. When the cylindrical container 11 is rotated counterclockwise, a test sheet 14 is delivered beneath the guide member 16 by forces of the test sheet pressing springs 7 and inserted into the through hole 15. Clockwise rotation of the cylindrical container 11 serves to press back the second and following test sheets, so that when the first test sheet drops, it will not be pressed and interfered by the second test sheet.

Figure 4:
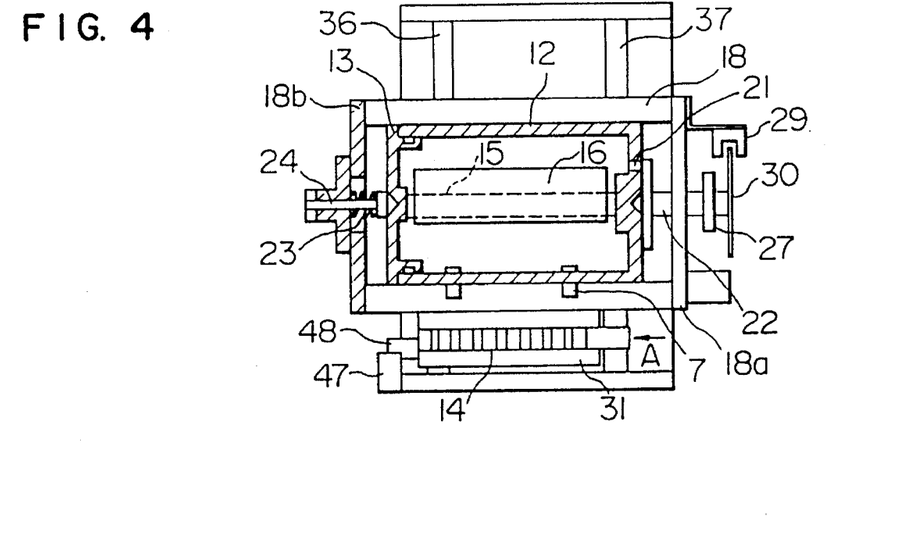
FIG. 4 is a cross-sectional view taken along the line IV—IV of FIG. 1.
Figure 5:
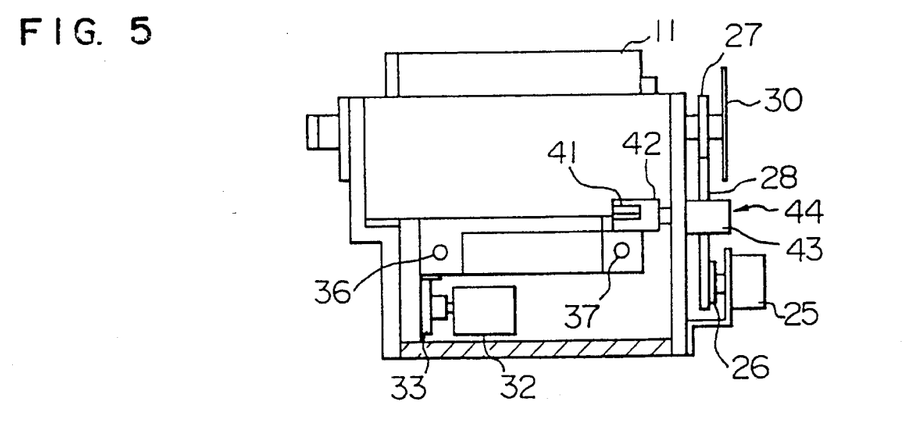
FIG. 5 is a front view showing the feeder of FIG. 1.

As shown in FIG. 4, the cylindrical container 11 is supported by a support shaft 22 having a motive power transmitting projection 21 for transmitting the rotational motive power and a movable support shaft 24 having a spring 23 which axially presses the container. The container is applied with the rotational force by the pulse motor 25, pulleys 26, 27 and a timing belt 28.

Referring again to FIG. 4, a rotational angle of reciprocal rotation of the container 11 itself (reciprocation around its own axis) is controlled by the control unit in response to signals produced from a notched disk 30 provided on the rotational shaft 22 of the rotational force transmitting mechanism and a notch position detector 29 attached to the fixed support 18. The rotational angle of reciprocation of the cylindrical container around its own axis is about 85 degrees clockwise and about 78 degrees or more counterclockwise.

The bottom of the container 11 is engaged with the motive power transmitting projection 21 of the rotational force transmitting mechanism (FIG. 4) whereas, the cover 13 of the container 11 is supported by the support shaft 24 provided with the pressing spring 23. Therefore, by pressing the container body 12 to the left as viewed in FIG. 4, the container body 12 is released from the engagement with the projection 21, and the container 11 can be removed in an upward direction. In the illustrated embodiment, only one through hole 15 is formed in the container 11. However, two or more through holes may be formed if necessary.

The longitudinal curved outer surface of the cylindrical container 11 is formed to slide on the curved inner surface of the container support 18. The container support 18 prevents the through hole 15 from being opened to the outside during rotation of the container 11. If the through hole 15 was opened to the outside, a test sheet would jump out of the through hole 15. Consequently, the support 18 is located to cover the entire area in which the through hole 15 rotates and moves during rotation of the container 11 so as to prevent a test sheet 14 from jumping out. Generally, the quality of the testing pieces 9 of the test sheets 14 contained in the container 11 are changed by the humidity over a long time period; and therefore, the inner space of the container 11 is maintained at a low humidity by the desiccant 17 (FIG. 3). However, in order to decrease entrance of the outside air into the container 11 via the through hole 15, the outer periphery of the container 11 is covered with the support 18 so that an area in which the through hole 15 moves will not be opened to the outside.

The support 18, serving as a member for preventing jumping out of the test sheets 14, covers the lower outer-peripheral surface of the container 11. However, since the test sheets 14 must be taken out from the lower surface, a test sheet pass hole 20 through which the test sheets 14 are passed from the through hole 15 to the delivery stage 31 (FIG. 1, 2 and 8) is formed in the support member 18 at a location corresponding to the position of the through hole 15 when rotation of the container 11 is stopped. The hole 20 is closed by the shutter mechanism 45 during rotation of the container 11 and is opened when a test sheet 14 is dropped from the container 11. The dropped test sheet 14 is received in a test sheet receiving recess 38 formed on the test sheet delivering stage 31 which can be slid and moved. Side wall members 18a, 18b located on both sides of the member which forms the curved concave surface of the container support 18 support the rotational force transmitting mechanism. The test sheet pass hole 20 is bored in a central portion of the semi-cylindrical curved wall. Preferably, the cylindrical container 11 for containing the test sheets 14 is made of a light transmitting material such as acrylic resin. The illustrated support 18 is formed in such a manner that the reciprocal rotation angle of the container 11 is 90 degrees clockwise and 90 degrees counterclockwise, and the upper side of the support 18 is opened to allow the container 11 to be removed upward.

Separation means for separating a plurality of test sheets 14 from one another is provided in a passage portion of the test sheet delivering stage 31. As shown in FIG. 3, a blocking wall 50, constituting the separation means, is provided on a lower portion of the container support 18 and located in the axial center of the container support 18 while projecting downwardly from the container support 18. Accordingly, the receiving recess 38 is formed to have a length, a width and a depth corresponding to the dimensions of the test sheet 14. In other words, the receiving recess 38 has a length and a width for receiving the test sheet 14, and a depth which is equal to the thickness $\underline{h}$ (FIG. 6b) of one test sheet in the longitudinal center of the receiving recess and which is equal to the height $3h$ of curvature of the test sheet on both ends of the receiving recess so that the depth gradually varies from the center to the opposite ends. With the above-described structure of the blocking wall 50 and the receiving recess 38, the blocking wall 50 restricts the size of the passage in which the test sheet 14 received in the test sheet receiving recess 38 on the test sheet delivering stage 31 is moved. More specifically, the height of the blocking wall 50 is determined to allow only one test sheet 14 to pass. Thus, if two or more test sheets 14 are fed to the test sheet receiving recess 38 from the cylindrical test sheet container 11, the upper test sheets 14 of the superposed test sheets abut against the blocking wall 50 to remain on the spot when the test sheets 14 mounted on the test sheet receiving recess 38 are transferred toward the outside supplying position A, and consequently, only the lowermost test sheet 14 is permitted to be separated and transferred to the outside supplying position A. Then, this test sheet 14 is delivered to the test sheet transfer means 53, and when the test sheet delivering stage 31 is returned beneath the through hole 15 again, the foregoing remaining test sheets are received in the test sheet receiving recess 38 thus emptied. While the received test sheets 14 are transferred toward the outside supplying position A by the test sheet delivering stage 31 again, only one test sheet 14 is separated by the blocking wall 50 and delivered to the test sheet transfer means 53. This series of actions are repeated until the plurality of test sheets 14 which have been simultaneously supplied from the cylindrical test sheet container 11 and removed from the test sheet receiving recess 38.

Figure 1:
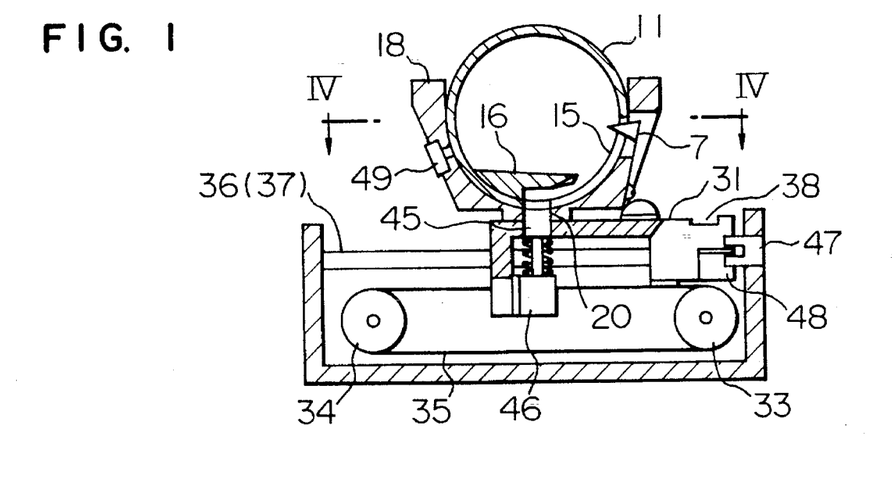
FIG. 1 is a vertical cross-sectional view of one embodiment of an analytic test sheet feeder according to the present invention.

The test sheet delivering stage 31 reciprocates horizontally along the guide shafts 36, 37 by the motor 32 (FIG. 5), the pulleys 33, 34 (FIG. 1) and the timing belt 35. The test sheet receiving recess 38 formed on the stage 31 receives test sheets 14 dropped from the test sheet pass hole 20 of the container support 18 above the receiving recess 38 and delivers it to the outside supplying position A. A side detector 40 FIG. 2) for optically detecting both sides of a test sheet is provided below the test sheet receiving recess 38. Also, there is provided a side reversing mechanism 44 consisting of a rotor 42 having a slot groove 41 facing the transfer passage of the delivering stage 31, and a motor 43 (FIG. 5) for driving the rotor 42. If a test sheet 14 faces the wrong side, the rotor 42 is rotated for 180 degrees when a handle portion of the test sheet 14 is located in the slot groove 41, so that the test sheet 14 is reversed to face the right side. The shutter 45 (FIGS. 1 and 2) is provided for opening/closing the test sheet pass hole 20 of the container support 18 and is operated by a solenoid 46. A detector 47 and a detecting terminal 48 shown in FIG. 1 are provided for determining the stop position of the delivering stage 31.

In this embodiment, the number of test sheets which can be filled in the cylindrical container 11 at once is 200, and they are filled so that handle portions of the test sheets 14 are located on the bottom side of the container 11 (the right side in FIG. 4). The operation of this apparatus is started from the state shown in FIG. 1 in which the container 11 is mounted and the hole 20 of the container support 18 is closed by the shutter 45, and comprises the steps described below.

(1) By actuating the pulse motor 25, the cylindrical container 11 is reciprocally rotated several times, and one test sheet 14 is placed in the through hole 15 by the test sheet pressing springs 7. In this embodiment, the test sheet 14 can be placed in the through hole 15 almost without fail by reciprocally rotating the container 11 three times to the left and right. A detector 49 (FIG. 1) is provided for the confirmation of such placement.

(2) When the through hole 15 of the container 11 is aligned with the test sheet pass holes 20 of the container support 18, the test piece pass hole 20 is opened by pressing the shutter 45 downwardly, and the test sheet is caused to descend onto the delivering stage 31. In some cases, another test sheet 14 may follow the first test sheet 14, so that two test sheets 14 superposed may descend together.

Figure 2:
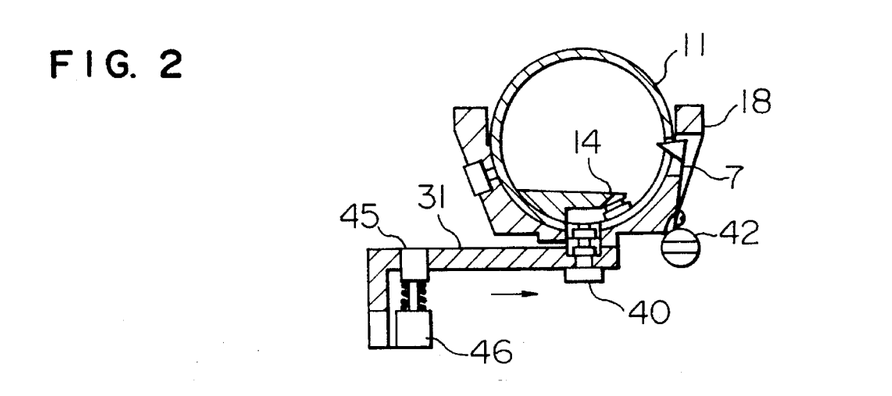
FIG. 2 is a cross-sectional view for explaining the operation of the feeder shown in FIG. 1.

(3) By moving the delivering stage 31 backwardly (to the left in FIG. 1), the test sheet receiving recess 38 is located under the test sheet pass hole 20, and the lowered test sheet 14 is dropped and placed in the test sheet receiving recess 38 (FIG. 2).

(4) The delivering stage 31 is moved forwardly (in a direction indicated by the arrow in FIG. 2), and the test sheet is delivered to the outside supplying position A. At this time, the second test sheet 14 superposed on and lowered with the first test sheet 14 abuts against the blocking wall 50 (FIG. 3) provided below one side of the test sheet pass hole 20 for prevention of movement, so that the second test sheet 14 remains in the test sheet pass hole 20 or the outlet.

(5) While delivering the test sheet 14, the side detector 40 judges whether the test sheet 14 faces the right side or not. If the test sheet 14 faces the wrong side, the side reversing mechanism 44 functions to make the test sheet 14 face the right side (FIG. 3).

(6) When the test sheet reaches the outside supplying position A, the shutter mechanism 45 is returned to the position corresponding to the test sheet pass hole 20. Then, the solenoid 46 is actuated to press the remaining test sheet upwardly and return the test sheet into the container 11, and also, the test sheet pass hole 20 is closed. In order to take out the next test sheet, the operation is restarted.

By repeating the above-described operation, the test sheets 14 filled in the cylindrical container 11 can be continuously sent out automatically to the test sheet supplying position. When the apparatus of this embodiment is used for an automatic urine analyzer, it can supply one test sheet every twelve seconds.

In the embodiment described above, the side detector 40 and the side reversing mechanism 44 of the test sheets 14 perform important functions. However, their forms and means are not necessarily limited to those of the foregoing embodiment. For example, without providing the automatic feeder with these functions, a robot mechanism for delivering test sheets 14 to an analysis unit from the tester outside sheet supplying position a may be designed to have a side reversing function.

Moreover, in the above-described embodiment, the step (6) may be replaced by the following operation in the step (4) although not illustrated in the drawings: The existence of the second and following test sheets 14 remaining in the test piece pass hole 20 or the outlet is detected by the side detector 40. When the second and following test sheets 14 exist, the test sheet 14 delivering stage 31 is moved below the test piece pass hole 20. Thus, the remaining test sheets 14 are permitted to freely drop and to be received in the test sheet receiving recess 38, and are transferred to the outside supplying position A. This operation is repeated until the remaining test sheets are removed from the test sheet receiving recess 38. After that, the step (1) and the subsequent steps are repeated. In this case, the existence of the second and following test sheets 14 is judged by the side detector 40. A reflection type optical sensor is used for the side detector 40. The output of a light emitting element strikes against a test sheet 14, and the reflected light is received by a light receiving element. There is utilized the fact that the output level of the side detector 40 in the absence of test sheets 14 is extremely close to zero, unlike the output level for detecting the both sides of a test sheet 14.

According to the present invention, test sheets 14 can be positively supplied one by one. Also, by supplying test sheets 14 one by one, it is possible to prevent errors in operating the automatic machine at the downstream side of the feeder, which occur when two or more test sheets 14 are supplied at once.

What is claimed is:

1. An analytic test sheet feeder comprising:

a container containing therein a plurality of analytic test sheets;

a first separator for separating individual test sheets from the container;

a storage disposed outside and below the container for receiving and storing the separated test sheets which are fed into the storage from the container by way of an opening in said analytic test sheet feeder;

shutter means movable for opening and closing said opening for respectively permitting or blocking the movement of individual test sheets from said container to said storage through said opening;

test sheet delivery means for moving the storage in a first direction to deliver the stored test sheets outside the analytic test sheet feeder;

a gate means disposed in a passage, through which the storage passes when moving outside of the analytic test sheet feeder, having a height, extending between a bottom of a test sheet receiving means of the storage and a surface of the passage through which the storage passes, which is greater than one but less than a thickness of two test sheets to prevent a plurality of test sheets stored in the storage from passing through the passage while allowing only a lowermost test sheet stored in the test sheet receiving means to pass through the passage, the storage having an extension rearwardly of the test sheet receiving means sufficient for receiving at least one test sheet which the gate means has not allowed to pass through the passage during movement in the first direction and which rests on the extension while sliding thereon during motion of the storage in the first direction;

the test sheet receiving means reciprocating back in a second direction opposite the first direction at least once to receive the at least one test sheet which has been initially prevented from passing through the passage by the gate means to pass the at least one test sheet through the gate means to outside the analytic test sheet feeder;

a detecting means for detecting if at least one test sheet is on the test sheet receiving means when the storage returns to below the container; and control means controlling the operation of said shutter means and said test sheet delivery means such that when at least one test sheet is detected as remaining in the test sheet receiving means the first separator is prevented by the detecting means from separating the test sheets from the test sheet container, the shutter means is prevented from closing said opening and the detecting means enables the test sheet delivery means to move the storage entirely outside of the analytic test sheet feeder to deliver any test sheets remaining in the test sheet receiving means outside of the analytic test sheet feeder.

* * * * *